United States Patent [19]

Carter

[11] Patent Number: 5,431,663
[45] Date of Patent: Jul. 11, 1995

[54] MINIATURE ULTRASONIC TRANSDUCER FOR REMOVAL OF INTRAVASCULAR PLAQUE AND CLOTS

[75] Inventor: Robert E. Carter, Arlington, Mass.

[73] Assignee: Coraje, Inc., San Francisco, Calif.

[21] Appl. No.: 164,255

[22] Filed: Dec. 8, 1993

Related U.S. Application Data

[62] Division of Ser. No. 625,919, Dec. 10, 1990, Pat. No. 5,269,291.

[51] Int. Cl.[6] .............................................. A61B 17/22
[52] U.S. Cl. ...................................... 606/128; 604/22
[58] Field of Search .................. 128/24 AA; 606/128, 606/169; 604/22; 601/2, 3

[56] References Cited

U.S. PATENT DOCUMENTS

| | | | |
|---|---|---|---|
| 3,990,452 | 11/1976 | Murry et al. ................. | 128/24 AA |
| 4,808,153 | 2/1989 | Parisi ............................ | 604/22 |
| 4,827,911 | 5/1989 | Broadwin et al. ........... | 128/24 AA |
| 5,069,664 | 12/1991 | Guess et al. ................. | 604/22 |
| 5,095,890 | 3/1992 | Houghton et al. ........... | 128/24 AA |

*Primary Examiner*—Ruth S. Smith
*Attorney, Agent, or Firm*—Walter A. Hackler

[57] ABSTRACT

Ultrasonic apparatus for clot dissolution and plaque ablation includes a radiator for coupling ultrasonic waves into plaque and a piezoelectric crystal, connected with said radiator, for the intravascular generation of ultrasonic waves; said ultrasonic waves being propagated along a longitudinal axis of said piezoelectric crystal and having an inertial node position within said piezoelectric crystal. The piezoelectric crystal is constructed in order to prevent significant power loss caused by a shifting of the inertial node of the generated ultrasonic waves to a position exterior to said piezoelectric crystal due to loading of the radiator-means caused by the coupling of ultrasonic waves into the clot or plaque.

8 Claims, 2 Drawing Sheets

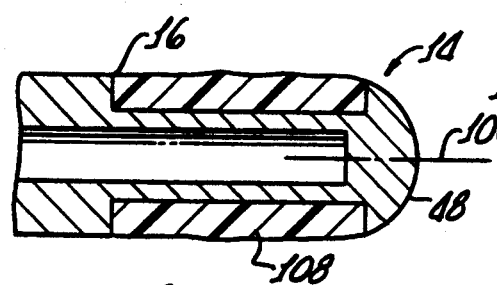
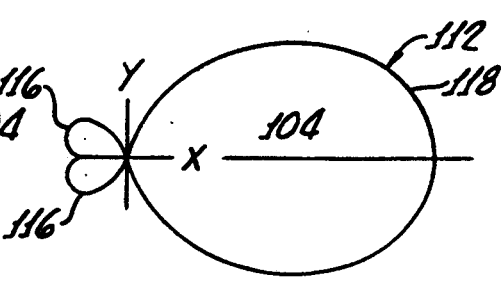
FIG. 4a.
FIG. 4b.
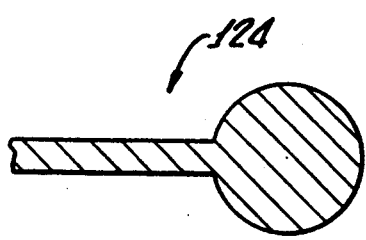
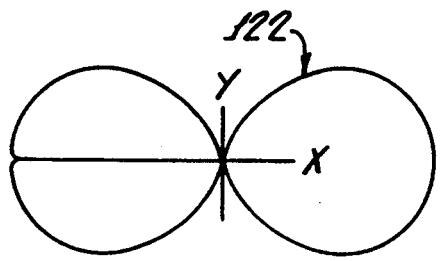
FIG. 5a.
(PRIOR ART)
FIG. 5b.
(PRIOR ART)
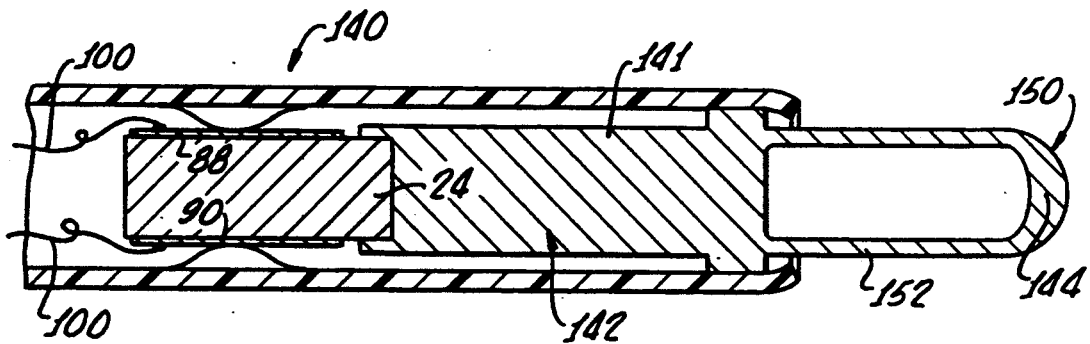
FIG. 6.

MINIATURE ULTRASONIC TRANSDUCER FOR REMOVAL OF INTRAVASCULAR PLAQUE AND CLOTS

This application is a division of U.S. patent application Ser. No. 07/625,919, filed Dec. 10, 1990, now U.S. Pat. No. 5,269,291.

The present invention is generally related to the use of ultrasonic energy for the ablation of atheroma and dissolution of blood clots in vessels and is more particularly directed to the intravascular generation of ultrasonic energy for removal of intravascular blockages by ablation thereof.

The accumulation of atheromas (atherosclerosis) or the formation of thrombi in a blood vessel may seriously impair circulation and if blockage occurs, distal tissues may be deprived of oxygen and nutrients, thereby resulting in disruption of cell tissue.

The thickening of atheroma reduces the elasticity of the blood vessel and significantly restricts the free passage of blood through a vessel, resulting in a stenosis such that even a small thrombus may become lodged, creating an infarct or occlusion.

A number of alternative methods and apparatus have been used in the treatment of arteriosclerosis and thrombosis. The treatment of stenotic and occlutic blood vessels depends in part on the severity of the blockage and the location thereof. In the case of coronary arteries, it is common to perform coronary bypass surgery to provide blood vessel shunts to restore blood flow past a severely blocked or occluded artery. This procedure is also utilized in deep vein thrombosis or other blockages in the peripheral vasculature.

As an alternative to surgery, balloon angioplasty has been utilized to expand accumulated deposits, or plaque. The method includes the insertion of an inflatable balloon, which is positioned at a stenosis and thereafter inflated to dilate stenotic arterial segments. This may obviate arterial bypass operations. However, balloon angioplasty has a number of limitations which include arterial dissection, bleeding, and reocclusion. In addition, re-stenosis is a common occurrence and near total blockages or occlusions are not treatable by balloon angioplasty techniques since the balloon cannot penetrate the occlusion.

Ultrasonic energy has been suggested for removal of intravascular blockages due to atherosclerotic plaque and intravascular blood clots. It has been shown that ultrasonic energy is useful in fragmenting plaque and thrombosis, either as a result of mechanical action thereon or cavitation thereof, in which high energy ultrasound applied to liquids generates vapor-filled microbubbles, or "cavities," with the concomitant rapid expansion and collapse of the cavities, accompanied by local intense hydraulic shock leading to fragmentation or dissolution of the thrombosis.

Heretofore developed equipment for the ultrasonic elimination of plaque and the like has included apparatus for the generation of the ultrasonic energy exterior to the body and the transmission of the ultrasonic energy into the body through a transmission wire to the stenosis site. Although good ultrasonic plaque ablation has been shown using an intravascular device consisting of a 2 mm titanium ball which is vibrationally excited by a 0.015 inch (0.38 mm) diameter titanium wire, these devices do not allow deployment in desired regions due to the stiffness of the transmission wire.

Unfortunately, when the wire diameter is reduced to lower the stiffness thereof, it can no longer deliver sufficient energy to the ball for surgical procedures.

The apparatus of the present invention eliminates the use of ultrasonic transmission wires by providing in situ generation of ultrasonic energy and direct ultrasonic radiation therefrom, which is capable of ablating plaque and dissolving clots even when the artery is totally occluded and which can be safely deployed in the arterial region of the heart itself.

SUMMARY OF THE INVENTION

In accordance with the present invention, ultrasonic apparatus for clot dissolution and plaque ablation includes radiator means for coupling ultrasonic waves into plaque and piezoelectric crystal means connected with the radiator means, for generating ultrasonic waves. The ultrasonic waves are of two types: standing waves and travelling waves. The standing waves are large in amplitude and are typified by observable inertial nodes (i.e., loci along the longitudinal axis of the transducer which remain nearly stationary during vibration at the resonant frequency), and inertial anti nodes (i.e., loci which represent local maxima of vibrational motion). The travelling waves are not easily observable, being a slight perturbation to the standing wave, yet they are responsible for all the energy flow supplied to the radiator.

In the present invention, an inertial node is positioned within the piezo crystal means, an an anti node is positioned at the radiator site. Importantly, the radiator means and the piezoelectric crystal means connected thereto are sized for intravascular positioning. This eliminates the need for stiff acoustic energy transmission lines heretofore used with prior art devices land the restricted treatment zones associated therewith.

Further, in accordance with the present invention, means are provided for preventing acoustic power transmission in unwanted directions.

In addition, in accordance with the present invention, means are provided which define the length of the piezoelectric crystal for preventing loss of acoustic power output caused in part by a shifting of the inertial node of the generated ultrasonic waves to a position exterior to the piezoelectric crystal due to a loading of the radiator means caused by coupling ultrasonic waves into plaque. In other words, the crystal length provides a means for enabling the piezoelectric crystal to sustain relatively constant ultrasonic vibrational amplitude at the radiator site, even as the radiator means couples ultrasonic energy into a variety of loads.

More particularly, the apparatus of the present invention may include amplifier means, interconnected between the radiator means and the piezoelectric crystal means, for transmitting and amplifying mechanical vibration at an ultrasonic frequency from the piezoelectric crystal means to the radiator means.

In one embodiment of the present invention, the radiator means includes a convex hemispherical radiating surface subtended by a concave hemispherical surface, having larger radius of curvature. The amplifier may be a single piece consisting of two solid cylindrical sections having different diameters, which are coaxial to both piezo and radiator. The amplifier means and the radiator means may be formed from a single piece of material.

In addition, the amplifier means and radiator means may include means defining a coaxial bore therethrough which extends from the piezoelectric crystal means to the concave surface of the radiator means. The hole may also extend through the piezo. The purpose of the hole is for a guide wire for suction.

Means may be provided for blocking ultrasonic energy which may radiate from the amplifier cylindrical body portion and the concave surface of the radiator means. More specifically, this means for blocking may include a low density foam material disposed over the cylindrical body portion of the concave surface and extending from the arcuate surface edge to the amplifier means cylindrical member. The foam material must have a specific acoustic impedance substantially less than that of the cylindrical body portion.

In another embodiment of the present invention, the amplifier means may include a single piece consisting of a solid cylindrical portion joined coaxially to a hollow cylindrical portion of equal outer diameter. The hollow cylindrical section is joined smoothly to the conex contour of the radiator to aoid sharp edges that might scratch the artery wall. It has now been found that this construction prevents back and side radiation. In addition, a catheter may be included, having at least one lumen therethrough and adapted for intravascular positioning with an ultrasonic transducer disposed in the catheter lumen at a distal end thereof.

The ultrasonic transducer may include radiator means for coupling ultrasonic waves into plaque and piezoelectric crystal means, connected with the radiator means, for generating ultrasonic waves which are propagated along a longitudinal axis of the piezoelectric crystal means with an inertial node positioned within the piezoelectric crystal means. Means are provided which include a length of the piezoelectric crystal for preventing power loss which may be caused by a shifting of the inertial node of the generated ultrasonic waves to a position exterior to the piezoelectric crystal means due to a loading of the radiator means caused by coupling of ultrasonic waves into plaque.

In addition, electrical power source means, disposed exterior to a proximate end of the catheter, and electrically connected to the ultrasonic transducer through the catheter lumen, is provided for causing a piezoelectric crystal to generate ultrasonic waves.

BRIEF DESCRIPTION OF THE DRAWINGS

A better understanding of the present invention may be had with the consideration of the following detailed description, taken in conjunction with the accompanying drawings in which:

FIGS. 4a and 4b are respectively a diagram of the ultrasonic apparatus shown in FIG. 3 and a plot of the acoustic radiation intensity generated thereby; and FIGS. 5a and 5b are respectively a diagram of prior art radiator and a plot of acoustic radiation intensity generated thereby;

FIG. 6 is a cross-sectional view of an alternative embodiment of a transducer in accordance with the present invention.

DETAILED DESCRIPTION OF THE DRAWINGS

Figure 1:
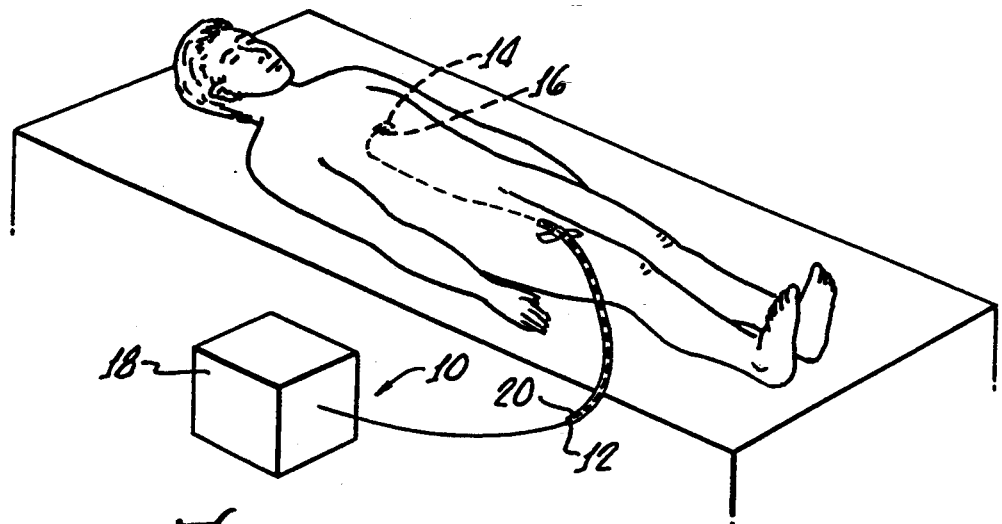
FIG. 1 is a diagram of ultrasonic surgical apparatus in accordance with the present invention for clot and plaque ablation, generally showing a catheter, an ultrasonic transducer disposed within a catheter lumen, and a power source disposed exterior to a proximate end of the catheter and electrically connected to the ultrasonic transducer through the catheter lumen.

Turning now to FIG. 1, there is shown ultrasonic surgical apparatus 10, generally including a catheter 12, an ultrasonic transducer 14, disposed at a distal end 16 of the catheter 12, and a power source 18 disposed exterior to a proximate end 20 of the catheter 12 and electrically connected to the ultrasonic transducer 14 for causing a piezoelectric crystal 24 (see FIG. 2) to generate ultrasonic waves as hereinafter described in greater detail. It should be appreciated that the catheter 12 and power source 18 may be of any conventional design suitable for use with the ultrasonic transducer 14, with the expected operating frequencies between about 50 kHz and 1.3 MHz, suitable for clot or plaque ablation.

It is well known that attendant to the coupling of ultrasonic energy into a medium, a shift in the locus of standing wave amplitude occurs which results in a significant reduction of the amplitude thereof and corresponding reduction in energy coupled to the load.

Figure 2:
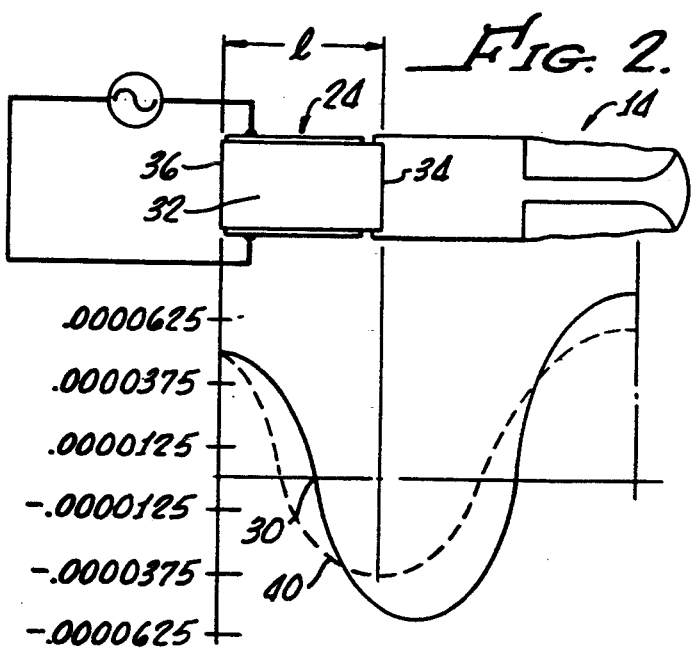
FIG. 2 is a diagrammatic view of ultrasonic apparatus in accordance with the present invention, generally showing a piezoelectric crystal connected with a radiator and a corresponding plot of an ultrasonic wave form generated thereby in an unloaded state (solid line) and a loaded state (dashed line)

When maintaining resonant vibration of transducer in an unloaded state, a piezoelectric crystal will generate a standing wave form as shown in the solid line of FIG. 2, which has an inertial node 30 which falls within the body 32 between a front face 34 and a rear face 36 thereof.

It has been discovered that when the piezoelectric crystal 24 length, 1, between the front and rear faces 34, 36 is of sufficient length, the inertial node 40 of the wave form representing the resonating transducer coupled to a load (dashed line), such as plaque or a blood clot, remains within the body 36 of the piezoelectric crystal 24, i.e., between the front face 34 and rear face 36. Under these conditions, significant power coupling loss of ultrasonic energy does not occur.

It is well known in the art that low power ultrasonic resonators (i.e., 20 watt power consumption at resonance under load), such as are used for surgical handpieces, must have all their parts manufactured to very tight tolerances in order to maintain capability of achieving high vibrational motion in air (i.e., unloaded). It is also well known that the addition of an undesigned mass or spring load to the tip significantly reduces the vibration amplitude at resonance, and the power delivery capability. However, it has been found that resonators constructed in accordance with the present invention, i.e., a piezoelectric crystal 24 having an entire end made from active piezoelectric material, and having an inertial node within the body of the ceramic do not need metal pieces with accurate tolerances in order to function. Furthermore, mass, spring, fluid, or point contact-type loads applied to the radiator do not generally cause a loss of amplitude at resonance but instead cause an increased power draw from the AC power supply used to drive the crystal.

Figure 3:
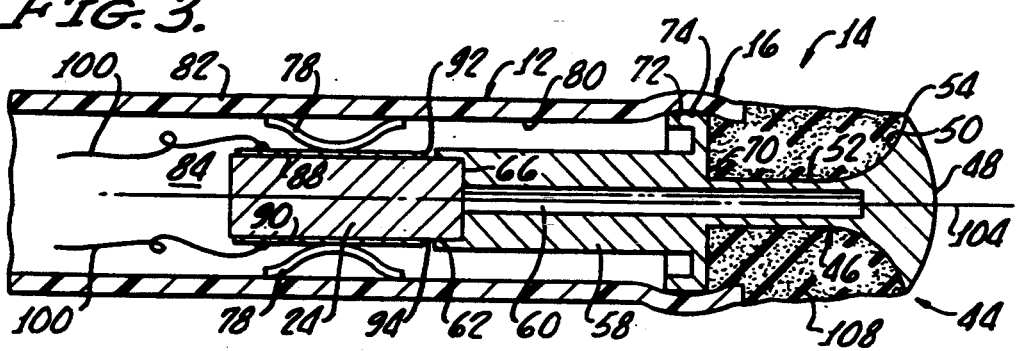
FIG. 3 is an enlarged cross-sectional view of ultrasonic apparatus in accordance with the present invention.

Turning now to FIG. 3, there is shown an enlarged view of the transducer 14 of the present invention disposed at the distal end 16 of the catheter 12.

A radiator 44 provides means for coupling ultrasonic waves into plaque (not shown) which includes a cylindrical body portion 46 and an arcuate convex radiating surface 48 which is subtended by a concave surface 50 extending from a surface 52 of the body portion 46 to an edge 54 of the arcuate radiating surface 48. The radius of the concave surface 50 may be greater than that of the radiating surface 48. It should be appreciated that while the radiating surface 48 is shown in the drawing with a generally hemispherical shape, a number of blunt shapes may be utilized as effective radiation of acoustic energy. As hereinafter described in greater detail, this structure, in part, provides for more efficient radiation of ultrasonic energy in a forward direction than prior art radiators. An amplifier 58 may be interconnected between the piezoelectric crystal 24 and the radiator 44 for transmitting and amplifying mechanical vibration of an ultrasonic frequency from the piezoelectric crystal 24 to the radiator 44.

With regard to nodal and frequency shift, it has been experimentally found that when operating at about 106 kHz, incidental contact of radiator to preserved artery samples causes a −1 kHz frequency shift. Immersion of the radiator tip in water causes a −2 kHz shift. It has been calculated that the nodal position shift with full embedding of the radiator 44 into bone-like material with a steady force applied to maintain contact is 2.5 mm when a 12.5 mm long crystal is used with a corresponding frequency shift of +16 kHz out of 104 kHz.

The radiator 44 and the amplifier 58 may be formed from a single piece of material, such as titanium. Titanium is a preferred material due to its lightweight nature and ability to vibrate longitudinally. Titanium is further known to be relatively non-lossy to sound waves. In addition, it is chemically inert and its hardness resists cavitation erosion. These characteristics make it preferable as a material for the radiator 44.

To enhance the transmission and amplification of ultrasonic waves from the piezoelectric crystal 24 to the radiating surface 48, a coaxial bore 60 may be formed or drilled into the amplifier 58 and body 46 from a back face 62 of the amplifier 58 to the concave surface 50. The effect of this bore is to increase the ratio of the cross-sectional area of the portion of the amplifier adjacent to the piezoelectric crystal 24 divided by the area of the portion adjacent to the radiator. In addition, an opening 66 may be formed in the back face 62 of the amplifier 58 for accepting the piezoelectric crystal 24, which typically would be square in cross-section.

Extending outwardly from a junction 70 of the body portion 46 of the radiator 44 and the amplifier 58 is a circular flange having an "L" portion 74 thereon, which provides means for centering the transducer 14 at the catheter distal end 16 and with the catheter lumen 76 with the body portion 46 and radiating surface 48 extending outwardly therefrom. In addition, a compliant support 78 may be provided adjacent to and surrounding the piezoelectric crystal 24 for supporting and centering the piezoelectric crystal 24 within the catheter lumen 76. The support 78 may be formed of any suitable material which would adhere to an inside wall 80 of the catheter, or the catheter wall 82 may be formed with a berm 78 to accomplish the purpose of supporting the piezoelectric crystal 24 in a centered coaxial relationship within the catheter lumen 76.

Electrodes 88 and 90 may be disposed on opposite sides 92 94 and interconnected by way of electrical leads 100 to the power source 18 as shown in FIG. 1. The electrodes 88 and 90, as well as the power source 18, may be of conventional design suitable for applying a voltage between the crystal faces 92, 94 in order to cause the mechanical generation of ultrasonic waves, the latter being propagated along a longitudinal axis 104 of the piezoelectric crystal 24. The piezoelectric crystal 24 may be of any suitable material well known in the art having piezoelectric characteristics such as lead zirconate titanate (PZT). Preferably the cross-section of the piezoelectric crystal 24 is square with a diagonal dimension of about 1 mm to about 6 mm, and for operating in a range of about 50 kHz to about 1.3 MHz, the length, l, of the piezoelectric crystal 24 would be about 1.25 mm to about 12.5 mm in order to sustain power output from the piezoelectric crystal 24 sufficient to maintain and cause cavitation for disruption and liquification of blood clots and plaque.

While the dimensions of the radiator 44 and amplifier 58 are empirically determined, in general the amplifier 58 length is greater than the piezoelectric crystal 24 and amplifier 58 diameter is comparable to the cross-sectional dimensions of the piezoelectric crystal 24. The radiator 44 diameter may be approximately equal to the piezoelectric crystal 24 diagonal dimension.

Turning again to FIG. 3, in order to reduce undesirable rearward or outward transmission of ultrasonic energy, a low density closed cell foam material 108 may be disposed over the cylindrical body portion 46 and concave surface 50. Preferably the foam material 108 has a very low specific acoustic impedance quantitatively similar to air. This provides a means for blocking the ultrasonic frequency radiating from the cylindrical body portion 46 and concave surface 50. The foam material 108 may extend from the arcuate surface edge 54 to the amplifier 58 and distal end 16 of the catheter 14. In addition, the foam material 108 also provides continuity between the arcuate edge 54 and the distal end 16 of catheter 12 to facilitate insertion and removal of the catheter 12 along with the transducer 14 from a vessel (not shown).

The structure of the transducer 14 in accordance with the present invention promotes the forward projection of acoustic waves along the longitudinal axis 104 as shown in FIGS. 4a and 4b, 4a being shown in reduced size and to correlate with the radiation pattern 12 shown in FIG. 4b. As shown, the rearward lobes 116 of the pattern 112 are considerably smaller than the forward lobes 118, and are considerably larger than the corresponding radiation patterns 122 shown in FIGS. 5a and 5b, FIG. 5a being representation of a prior art transducer 124. The improved radiation pattern shown in FIG. 4b is a result of eliminating all acoustic radiation paths in the region behind the forward radiating surface 148 by filling the region between the radiating surface 48 and the catheter distal end 16 with foam material 108.

Turning now to FIG. 6, there is shown an alternative transducer embodiment 140 in accordance with the invention. Like elements and features in the various figures are given the same reference number or other identification in FIG. 6.

The transducer 140 includes the piezoelectric crystal 24, electrodes 88 and 90, and electrical leads 100. A titanium amplifier 142 is interconnected between the piezoelectric crystal 24 and a radiator 144, the amplifier 142 and the radiator 144 preferably being one piece of material such as titanium. The amplifier 142 may include a substantially solid portion 141 and the radiator 144 may include a portion of lesser metallic cross-sectional area 152.

The radiator 144 may include a forward hemispherical surface 150. In this manner, the surface 152 eliminates a sideward and rearward emitting surface.

Experimental use of the hereinabove described transducers 14, 140 has established that when the transducer is held with the force of 60 grams against a submerged cross-sectional sample of totally occluded artery preserved in formaldehyde and the piezoelectric crystal 24 was driven with sufficient voltage at 100 kHz to produce a vibrational amplitude of 6.2 microns (peak) at the face, or tip, 150 of the radiator 144, steady penetration of the tip 150 into the plaque was observed. The resulting cavity was a smooth-walled imprint of the transducer tip 150.

With regard to the dissolution of blood clots, a sample of approximately 1 cubic centimeter in volume was removed from a large clot mass and submerged in a transparent plastic tray approximately 1 inch in diameter and ¼ inch deep. The transducer tip 150 was placed in a permanent position at a depth of about ⅛ inch in the center of the clot and energized as hereinabove described. A portion of the clot within a ¼ inch radius of the tip 150 was dissolved in two to three seconds.

Continued driving of the piezoelectric crystal 24 produced violent fluid motion and within one minute, the clot had separated into several pieces with each being propelled in eddied currents around the tray and aiming of the transducer at each piece resulted in complete dissolution within one additional minute. After a total lapsed time of about two to three minutes, the appearance of the fluid in the tray was indistinguishable with that of blood. In this experiment, the peak amplitude for clot dissolution was about 5 microns at 100 kHz; thus the voltage requirement is less for clot ablation than for slow plaque penetration.

Although there has been hereinabove described a specific arrangement of ultrasonic surgical apparatus for both blood clot and plaque ablation, in accordance with the present invention, for the purpose of illustrating the manner in which the invention may be used to advantage, it will be appreciated that the invention is not limited thereto. Accordingly, any and all modifications, variations, or equivalent arrangement which may occur to those skilled in the art should be considered to be within the scope of the invention as defined in the appended claims.

What is claimed is:

1. Ultrasonic apparatus for removal of intravascular blockages, including clots and plaque said ultrasonic apparatus comprising:
   radiator means for coupling ultrasonic waves into the intravascular blockage, said radiator means having a hollow cylindrical body portion and a hemispherical surface disposed at a radiating end thereof; and
   piezoelectric crystal means, connected with said radiator means, for the intravascular generation of ultrasonic waves having a frequency of between about 50 kHz and about 1.3 MHz, said ultrasonic waves being propagated along a longitudinal axis of said piezoelectric crystal means and having an inertial node position within said piezoelectric crystal means, said radiator means and piezoelectric crystal means being sized for intravascular positioning, said piezoelectric crystal having sufficient length to prevent significant power loss during loading of the radiator means caused by the coupling of ultrasonic waves into the intravascular blockage.

2. The apparatus according to claim 1 further comprising amplifier means, interconnected between said radiator means and said piezoelectric crystal means, for transmitting and amplifying mechanical vibrations of an ultrasonic frequency from said piezoelectric crystal to said radiator means, wherein said radiator means is metallic and said amplifier means having a larger metallic cross-sectional area than the metallic cross-sectional area of the radiator means.

3. The apparatus according to claim 2 wherein said amplifier means and radiator means are formed from a single piece of material.

4. Ultrasonic surgical apparatus for removal of intravascular blockage, including clots and plaque said ultrasonic apparatus comprising:
   a catheter having at least one lumen therethrough and adapted for intravascular positioning;
   an ultrasonic transducer disposed in the catheter lumen at a distal end thereof, said ultrasonic transducer comprising:
   radiator means for coupling ultrasonic waves into the intravascular blockage, said radiator means having a hollow cylindrical body portion and a hemispherical surface disposed at a radiating end thereof;
   piezoelectric crystal means, connected with said radiator means, for generating ultrasonic waves, having a frequency of between about 50 kHz and about 1.3 MHz, said ultrasonic waves being propagated along longitudinal axis of said piezoelectric crystal means and having an inertial node position within said piezoelectric crystal means, said piezoelectric crystal means having sufficient length, to prevent power loss during loading of the radiator means caused by the coupling of ultrasonic waves into the intravascular blockage; and
   power source means, disposed exterior to a proximate end of said catheter and electrically connected to said ultrasonic transducer through said catheter lumen, for causing said piezoelectric crystal to generate ultrasonic waves.

5. The apparatus of claim 4 further comprising amplifier means, interconnected between said radiator means and piezoelectric crystal means, for transmitting and amplifying mechanical vibrations of an ultrasonic frequency from said piezoelectric crystal means to said radiator means.

6. The apparatus according to claim 5 wherein said radiator means is metallic and said amplifier means comprises a cylindrical member having a larger metallic cross-sectional area than the metallic cross-sectional area of the radiator means.

7. The apparatus according to claim 6 wherein said amplifier means and radiator means are formed from a single piece of material.

8. The apparatus according to claim 7 wherein said cylindrical body portions and radiator surface are disposed exterior to the catheter distal end.

* * * * *